United States Patent [19]

Miyata et al.

[11] Patent Number: 4,806,683

[45] Date of Patent: Feb. 21, 1989

[54] PREPARATION PROCESS OF CINNAMIC ACIDS

[75] Inventors: Katsuharu Miyata, Yokohama; Usaji Takaki, Fujisawa; Toshio Matsuhisa, Shimonoseki, all of Japan

[73] Assignee: Mitsui Toatsu Chemicals, Incorporated, Tokyo, Japan

[21] Appl. No.: 16,736

[22] Filed: Feb. 20, 1987

[30] Foreign Application Priority Data

Feb. 28, 1986 [JP] Japan ................................ 61-41977

[51] Int. Cl.[4] ................................ C07C 63/64

[52] U.S. Cl. ................................ 562/495

[58] Field of Search ................................ 562/494, 495

[56] References Cited

U.S. PATENT DOCUMENTS 3,783,140 1/1974 Heck .

3,922,299 11/1975 Heck .

OTHER PUBLICATIONS

Organic Reactions, vol. 1 (1942), p. 217.

*Primary Examiner*—Michael L. Shippen

*Attorney, Agent, or Firm*—Fisher, Christen & Sabol

[57] ABSTRACT

A process is disclosed which prepares a cinnamic acid from a cinnamate ester by starting the hydrolysis reaction of the cinnamate ester with an alkali by use of water as a solvent in a heterogeneous binary-phase liquid system to obtain an aqueous alkaline solution of an alkali cinnamate and precipitating the cinnamic acid by conducting an acidifying reaction of said aqueous alkaline solution with a mineral acid so as to keep a pH value of not more than 4 in a resulting liquid.

4 Claims, No Drawings

PREPARATION PROCESS OF CINNAMIC ACIDS

BACKGROUND OF THE INVENTION (1) Field of the Invention

The present invention relates to a preparation process of cinnamic acids by the hydrolysis of a alkyl ester of the cinnamic acids.

Cinnamic acids are technically important as materials for perfumes, photosensitive polymers and various organic or biochemical products.

(2) Description of the Prior Art

Regarding the processes for the synthesis of cinnamic acid and its derivatives, a variety of methods has been known up to the present time.

For instance, these processes are methods of preparing cinnamic acid and its derivatives from benzaldehydes as a main raw material by Perkin reaction, Knoevenagel reaction or Claisen condensation (as described in, for example, Organic Reactions, vol. 1, 217 (1942)), and from benzene or its derivatives and acrylate esters as raw materials (as described in, for example, Japanese Patent Publication No. 50611/'72, Japanese Patent Laid-Open No. 59927/'83, U.S. Pat. No. 3,783,140 and U.S. Pat. No. 3,922,299). Besides a method has also been proposed recently wherein styrene or its derivatives are reacted with carbon monoxide, alcohol and oxygen in the presence of a catalyst (as described in Japanese Patent Publication Nos. 5570/'84 and 23661/'85).

Cinnamate esters are always formed as an intermediate in such processes as Claisen condensation which used benzaldehyde and acetate esters, a method of using benzene or its derivatives and acrylate esters as the raw materials, and a method of employing styrene or its derivatives, carbon monoxide, alcohol and oxygen as the raw materials. Therefore hydrolysis of cinnamate esters is necessary for preparing free cinnamic acids.

Concerning the hydrolysis of cinamate esters a method has recently been proposed which applies an acid as the catalyst (as described in Japanese Patent Laid-Open No. 112736/'85). The hydrolysis, however, is generally performed by use of alkali such as sodium hydroxide in a homogeneous system which contains aqueous mixture of alcohol, dioxane or acetone (as described in Japanese Patent Laid-Open No. 102614/'74).

On the hydrolysis of cinnamate esters with an acid catalyst a long reaction time is generally required because of a low reaction rate. On the other hand, the alkali hydrolysis is, as described above, carried out in a homogeneous system employing the aqueous mixture of organic solvents. Therefore, procedures such as extraction and concentration are required for the isolation of desired products. Furthermore, the solvents used for the extraction should be recovered in the industrial application.

Besides a step of acidifying the resultant alkaline solution with mineral acids after alakli hydrolysis is required in order to finally obtain the cinnamic acids.

In the prior arts, mineral acids are added to the aforesaid alkaline solution of alkali cinnamate containing the organic solvents.

In these cases, however, acidification must be performed in a low concentration which is diluted with a large amount of water as a result of employing a dilute aqueous alkali cinnamate solution, using a dilute aqueous solution of the acid or diluting the system with a special addition of water. Otherwise the system becomes a slurry having a high viscosity on the way of acidification and in extreme cases stirring is inhibited by the solidification of total system. Therefore it becomes difficult to conduct the acidification of aqueous solution of the alkali cinnamate with the mineral acid in a high concentration and the amount of products produced per unit volume of the reaction vessel is reduced.

Furthermore, the use of organic solvents described in the prior art results in the loss due to dissolving of desired product into the solvents and hence cause the reduction of yield.

SUMMARY OF THE INVENTION

An object of this invention is to provide an industrial method of preparing a cinnamic acid by the hydrolysis of a cinnamate ester with an alkali.

Another object of this invention is to provide a method of starting the hydrolysis reaction with the alkali in the absence of organic solvents and in the presence of water as the solvent in a heterogeneous binary-phase liquid system.

A further object of this invention is to provide a method of preparing the cinnamic acid by starting the hydrolysis of the cinnamate ester with the alkali in the heterogeneous binary-phase liquid system, followed by acidifying the resultant alkaline solution with the mineral acid through an improved method.

The present inventors have made an intensive effort on the study of alkali hydrolysis of cinnamate esters to achieve the objects described above. As a result, it has been found that the cinnamic acid having an excellent quality can be favorably obtained by alkali hydrolysis in the heterogeneous binary-phase liquid system with the aqueous solvent in the absence of organic solvents, and followed by acidifying the resultant aqueous alkaline solution so that the pH value of the solution obtained by the reaction was not more than the specific value.

Besides the following facts have also been found. When the acidification of aforementioned aqueous alkaline solution is conducted either by adding the aqueous alkaline solution into the mineral acid or by continuously charging the aqueous alkaline solution and said mineral acid into the reaction vessel so as to keep the pH value at not more than the specific value in the mixture obtained by acidifying and continuously discharging the product, this method can decrease the quantity of water in use, and thus the amount of product produced per unit volume of the reaction vessel can be increased, the environmental problems on drainage is mitigated, the loss of the product by dissolving in the drainage is reduced and the cinnamic acids having an excellent quality can be obtained in good efficiency.

That is, the present invention is a process of preparing a cinnamic acid by the hydrolysis of a cinnamate ester with an alkali which comprises starting the hydrolysis reaction of the alkyl cinnamates with the alkali in the heterogeneous binary-phase liquid system with an aqueous solvent in the absence of organic solvents, and acidifying the resultant aqueous alkaline solution so as to obtain the pH value of not more than 4 in the solution after acidification.

More preferably, the present invention includes a process for preparing the cinnamic acid which comprises either adding the aqueous alkaline solution obtained by the alkali hydrolysis of the cinnamate ester into the mineral acid, or continuously charging the aqueous alkaline solution and the mineral acid into the reaction vessel to keep the pH value of not more than 4 in the solution after acidification and continuously discharging the reaction mixture.

According to the process of this invention, the hydrolysis of the cinnamic acid ester with the alkali can be started in the heterogeneous binary-phase liquid system with the aqueous solvent in the absence of organic solvents. Therefore, recovery of the organic solvents is not required and easy separation of the resultant cinnamic acid can be attained.

Besides in accordance with the process of this invention, the aqueous alkaline solution of the alkali cinnamate obtained by the alkali hydrolysis of the cinnamic acid ester can be acidified at a high concentration, the quantity of products per unit volume of the reaction vessel can be increased, the quantity of water in use can be reduced, the environmental problems of drainage can be mitigated and the loss by dissolving the products into the drainage can be decreased. Hence the cinnamic acid having good quality can be obtained efficiently and in good yield.

Therefore the method of this invention is technically very advantageous for preparing the cinnamic acid.

DETAILED DESCRIPTION OF THE INVENTION

The cinnamate esters useful for the practise of the process of this invention are represented by the following formula:

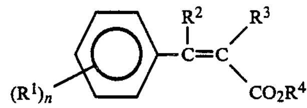

(wherein n is an integer of 1 to 5, $R^1$ is hydrogen or at least one kind of substituent on the aromatic ring and represents, for example, halogen, hydroxyl, alkyl of 1 to 4 carbon atoms or alkoxy of 1 to 4 carbon atoms, and where n is not less than 2, each $R^1$ is the same or different. $R^2$ and $R^3$ may be the same or different groups and represent respectively hydrogen or alkyl of 1 to 6 carbon atoms.

$R^4$ represents unsubstituted or substituted alkyl group.)

The cinnamate esters include, for example, methyl cinnamate, ethyl cinnamate, propyl cinnamate, butyl cinnamate, ethyl α-methyl-β-phenylacrylate, methyl α-propyl-β-chlorophenylacrylate, methyl β-3,4-dimethoxyphenylacrylate, methyl β-4-methoxyphenylacrylate and benzyl cinnamate.

The cinnamate esters mentioned above can be prepared by various methods. For example, as aforesaid, these can be prepared by Claisen condensation from benzaldehydes and acetate ester, by the oxidative carbonylation reaction of styrene compounds, by the reaction of benzene or its derivatives with acrylate ester and further by the separation from natural storax.

The alkali for use in the alkali hydrolysis of this invention includes, for example, sodium hydroxide, potassium hydroxide, calcium hydroxide and barium hydroxide. Sodium hydroxide or potassium hydroxide is preferably employed among these compounds. The alkali can also be applied as a mixture of two or more. The quantity of alkali in use is at least one equivalent to the cinnamate ester.

The hydrolysis reaction of cinnamate esters with alkali in the process of this invention is started in the heterogeneous binary-phase liquid system which consists of melted cinnamate ester and aqueous alkali solution. Although alkali cinnamates formed in the hydrolysis are rather easily dissolved in water, insufficient quantity of water in use causes incomplete dissolution. As a result a homogeneous solution cannot be formed and in the extreme cases the operation is substantially inhibited as a result of solidification. While excessive quantity of water leads to the reduction of yield.

Therefore, for the technically effective application of the method of this invention, it is required to use water in such quantity that the concentration of the alkali cinnamate is 1 to 20% by weight in the aqueous solution. It is preferably in the range of 2 to 15% by weight.

For the hydrolysis reaction of the cinnamate ester with aqueous solution of the alkali, any operation can be applied which includes a batchwise or semibatchwise operation of charging both components in a lump or separately into the reaction vessel and a continuous operation of continuously charging these components.

The reaction temperature is preferably in the range of 40° to 120° C. and more preferably 60° to 100° C.

The reaction pressure is normally atmospheric and yet in some cases slightly decreased or increased pressure is effective.

The reaction time depends upon reaction temperature and pressure and is preferably in the range of 1 to 120 minutes, and more preferably 3 to 30 minutes.

Vigorous stirring is effective for the process of this invention because the hydrolysis reaction of the alkyl cinnamate with the alkali starts in the heterogeneous binary-phase liquid system except that special cinnamate esters are used as raw materials. The mixture generally forms a homogeneous solution after ending the reaction In the method of this invention, alcohols generated in the course of the hydrolysis reaction may optionally be recovered, for example, by distilling from the system during or after the reaction.

An example of the effective manner for removing alcohol is to distill generated alcohol out of the system together with exhaust gas by feeding inert gas into the reaction solution.

In the process of this invention, the cinnamic acids can be precipitated by acidifying the resultant aqueous alkaline solution with the mineral acid and the reaction mixture forms a slurry or suspension. The cinnamic acids can be separated from the mixture by suitable means, for example, filtration, decantation and the like.

Water soluble mineral acid which is usually available in industry can be used in the acidification of the alkali cinnamate solution. The mineral acid includes, for example, hydrochloric acid, sulfuric acid and phosphoric acid In order to afford high yield of the cinnamic acid in the method of this invention, the alkali cinnamate and the mineral acid are required to react so as to keep the pH value at not more than 4 and preferably at not more than 3 in the solution after ending the acidification reaction.

When the pH value is more than 4, precipitation of the desired product is incomplete even in acidic conditions and thus the yield is reduced. Therefore the acidification reaction of the alkali cinnamate solution is suitably carried out by maintaining the system always in acidic conditions, that is, at the pH value of not more than 4 and preferably not more than 3.

In the process of this invention, the acidification of aqueous alakline solution of the alkali cinnamate can be performed by the batchwise, semi-batchwise or continuous operation. The embodiments of acidification reaction are, for example, the operation of adding said mineral acid into the aqueous alkaline solution of alkali cinnamate, the operation of adding the aqueous alkaline solution of alkali cinnamate into the mineral acid and the operation of continuously charging both components. Any of these operations can be applied.

In the operation of adding the mineral acid into the aqueous solution of alkali cinnamate, however, the reaction mixture often forms a slurried liquid having a high viscosity. In the extreme cases the stirring is inhibited. As a result the product is deteriorated in quality and the yield tends to decrease.

Therefore, to avoid aforesaid problems in the batchwise or semi-batchwise operation, the alkaline solution of alkali cinnamate is preferably added into the mineral acid.

Besides the acidification reaction of this invention is also preferably conducted by the continuous operation. The term continuous operation mentioned herein is different from what is called batchwise operation in which raw materials are charged in a lump and discharged after ending the reaction. It means the operation of discharging the reaction product while charging the raw materials. The charge or discharge operation may not always be continuous. The operation may be intermittent with a suitable interval so long as the operation does not make this invention invalid.

For example, quantity of the raw materials can be set so as to obtain the pH value of not more than 4 after the reaction. And the materials may be fed continuously or intermittently at a certain rate.

On conducting the acidification reaction of this invention, the continuous reaction may optionally be started after previously charging the sufficient quantity of aqueous solution of the mineral acid for stirring the reactant. Vigorous stirring is more effective for the acidification.

The suspension of the cinnamic acid formed by the acidification of this invention is continuously discharged, and optionally, it may be discharged intermittently. As a concrete method, for example, from a flooding port equipped on the reaction vessel, the suspension may be discharged by an overflow mode, or may also be discharged by use of a pump.

The separation step of the cinnamic acid from the suspension may be carried out batchwise or continuously.

In the acidification reaction of aqueous alkaline solution of the alkali cinnamate by the method of this invention, the quantity of water in use is adjusted so that the concentration of the produced cinnamic acid is preferably 1 to 20% by weight and more preferably 2 to 15% by weight of the suspension. The concentration outside of this range cannot sufficiently achieve the object of this invention. That is, the yield of the product reduces at less than 1% by weight, while a highly concentrated slurry is formed at more than 20% by weight and causes insufficient stirring, incomplete reaction and deterioration in the purity of product.

In the acidification of this invention, the batchwise or semi-batchwise operation wherein the aqueous solution of alkali cinnamate is added into the mineral acid, or the continuous operation wherein the reaction is conducted by maintaining the pH value of the system at not more than 4, has the advantage of performing the acidification in the higher concentration of the produced cinnamic acid in the suspension.

The temperature in the acidification reaction is suitably 10 to 80° C. The reaction is normally carried out under atmospheric pressure and may also be performed under slightly reduced or increased pressure.

The present invention is further illustrated by the following Examples and Comparative examples.

EXAMPLE 1

A separable flask equipped with a stirrer was charged with 16.2 grams (0.10 mol) of methyl cinnamate, and a solution of 4.3 grams of 97 wt. % sodium hydroxide in 200 grams of water, and the mixture was reacted at 80° C. for 15 minutes with vigorous stirring. The aqueous alkaline solution of sodium cinnamate thus obtained was added slowly under stirring with 200 ml of aqueous sulfuric acid solution containing 0.056 mol of sulfuric acid. The formed suspension had pH of approximately 1.5 after cooling to room temperature. The precipitates were filtered with suction, washed with 50 ml of water by stirring in a beaker, filtered again and dried under reduced pressure. Cinnamic acid thus obtained was 14.6 grams (98.5% yield) and had purity of more than 99.9% according to analysis.

COMPARATIVE EXAMPLE 1

The procedure of Example 1 was repeated except 64 grams of water were used in the hydrolysis. As a result, the reaction solution was entirely solidified at around 5 minutes after starting the hydrolysis reaction of methyl cinnamate with sodium hydroxide, and further proceeding of the reaction was failed.

COMPARATIVE EXAMPLE 2

The procedure of Example 1 was repeated except 2100 grams of water in the hydrolysis and 200 gram of aqueous sulfuric acid solution containing 0.08 mol of sulfuric acid were used in acidification. Consequently, cinnamic acid obtained was 13.8 grams and the yield was reduced to 93.2%.

COMPARATIVE EXAMPLE 3

The procedure of Example 1 was repeated except 2000 ml of aqueous sulfuric acid solution containing 0.085 mol of sulfuric acid were used in place of the aqueous acid solution in acidification. Consequently, cinnamic acid obtained was 13.9 grams and the yield wa reduced to 93.8%.

EXAMPLE 2

The same reaction procedure as in Example 1 was carried out except 230 grams of water was used in hydrolysis. After heating for 15 minutes with stirring, the flask was fitted with a Liebig's condenser and further heated to give 30 grams of distillate. The distillate contained 3.1 grams of methanol according to the analysis by gas chromatography.

EXAMPLE 3

The same reaction procedure as in Example 1 was carried out except 17.6 grams (0.1 mol) of ethyl cinnamate was used in place of methyl cinnamate. Consequently, cinnamic acid obtained was 14.5 grams (97.9% yield) and had purity of above 99.9%.

EXAMPLE 4

The procedure of Example 1 was repeated except 6.9 grams of 85% potassium hydroxide was used in place of sodium hydroxide in hydrolysis. Consequently, cinnamic acid obtained was 14.5 grams (97.9% yield) and had purity of above 99.9%.

EXAMPLE 5

The procedure of Example 1 was repeated except 0.112 mol of hydrochloric acid was used in place of 0.056 mol of sulfuric acid in acidification. Consequently, cinnamic acid obtained was 14.4 grams (97.2% yield) and had purity of above 99.9%.

EXAMPLE 6

A 300 ml separable flask was charged with 16.2 grams (0.10 mol) of methyl cinnamate, and a solution of 4.3 grams of 97 wt. % sodium hydroxide in 140 grams of water. The mixture was reacted at 80° C. for 15 minutes with vigorous stirring. The aqueous alkaline solution of sodium cinnamate thus obtained was poured into a hot funnel which was previously kept at 80° C. The solution was added dropwise with stirring to a beaker having 20 ml of aqueous sulfuric acid solution containing 0.053 mol of sulfuric acid. The resultant suspension was cooled to room temperature and filtered with suction. The crystals were washed with 50 ml of water by stirring in a beaker, filtered and dried under reduced pressure. Cinnamic acid obtained was 14.7 grams (99.9% yield). The purity was above 99.9% according to analysis.

EXAMPLE 7

The procedure of Example 6 was repeated except 17.6 grams (0.1 mol) of ethyl cinnamate was used in place of methyl cinnamate. Consequently cinnamic acid thus obtained was 14.6 grams (98.5% yield) and had purity of above of 99.9%.

EXAMPLE 8

The procedure of Example 6 was repeated except 6.9 grams of 85 wt. % potassium hydroxide in place of sodium hydroxide. Consequently cinnamic acid thus obtained was 14.5 grams (97.9%) and had purity of above 99.9%.

EXAMPLE 9

The procedure of Example 6 was repeated except 0.102 mol of hydrochloric acid was used in place of 0.053 mol of sulfuric acid in acidification. Consequently cinnamic acid thus obtained was 14.4 grams (97.2% yield) and had purity of above 99.9%.

EXAMPLE 10

A 1 l round bottomed flask equipped with a stirrer was charged with 100.0 grams (0.617 mol) of methyl cinnamate and 700 grams of aqueous solution containing 25.9 grams (0.647 mol) of sodium hydroxide and vigorously stirred for 15 minutes at 80° C. Then the resultant aqueous alkaline solution of sodium cinnamate having concentration of 13.1% by weight was transferred to a hot dropping funnel kept at 80° C.

A round bottomed flask having an overflow port of about 20 mm in diameter in the middle of the vessel (the volume below the port was about 130 ml) was respectively equipped with a stirrer, an electrode of pH meter, a discharge orifice of tube pump capable of delivering 25 wt. % aqueous sulfuric acid solution at a constant flow rate, and an orifice of hot dropping funnel containing aqueous alkaline solution of sodium cinnamate.

After charging about 20 grams of sulfuric acid in the flask in advance, the aqueous alkaline solution of sodium cinnamate was added dropwise with stirring until pH of 2 was indicated. Then the aqueous solution of sodium cinnamate and 25 wt. % aqueous sulfuric acid solution were added dropwise at a rate of 13 grams per minute and 2.0 grams per minute respectively. The reaction was always carried out at the pH of not more than 2 and terminated after one hour. The concentration of cinnamic acid in the reaction vessel was about 10 wt. %.

The slurry flowed out of the overflow port and cinnamic acid finally remained in the flask were filtered with suction, washed with water and dried under reduced pressure. Cinnamic acid thus obtained was 90.0 grams (98.5% yield) and had purity of above 99.9% according to the analysis of liquid chromatography. The quantity of cinnamic acid produced was 116 g/l to one liter of water used, and about 700 g/l to the unit volume of reaction vessel.

An aqueous alkaline solution of sodiu cinnamate was obtained by the same method as described above. The solution was distilled at about 100° C., a fraction of 98 to 99° C. was collected, and 17.8 grams of methanol were recovered as an aqueous solution.

COMPARATIVE EXAMPLE 4

A 3 l flask equipped with a stirrer was charged with 100.0 grams (0.617 mol) of methyl cinnamate and 1260 grams of aqueous solution containing 25.9 grams (0.647 mol) of sodium hydroxide and vigorously stirred for 15 minutes at 80° C. The obtained aqueous alkaline solution of sodium cinnamate having concentration of 7.7% by weight was added in a lump with 1240 ml of aqueous sulfuric acid solution containing 0.35 ml of sulfuric acid. The resultant slurry having concentration of 3.4% by weight was cooled to room temperature and measured pH to give a value of about 2. The total reaction mixture was discharged and filtered with suction. The separated precipitates were 87.8 grams (96.0% yield) and had purity of above 99.9%. The quantity of cinnamic acid produced per l of water used and per unit volume of the reaction vessel were 36 g/l and 35 g/l respectively.

EXAMPLE 11

The procedure of Example 10 was repeated except 19 wt. % hydrochloric acid was used in place of 25 wt. % sulfuric acid and pH was kept at not more than 3 in the reaction vessel in acidification. Consequently cinnamic acid obtained was 89.5 grams (97.9% yield) and had purity of above 99.9%.

COMPARATIVE EXAMPLE 5

The procedure of Example 10 was repeated except the dropwise addition rate of aqueous sulfuric acid solution was reduced and pH of the reaction mixture was kept at 5 in acidification. As a result, the separated cinnamic acid was 85.5 grams and the yield was reduced to 93.5%.

What is claimed is:

1. In a process of preparing a cinnamic acid by the hydrolysis of a cinnamate ester with an alkali, the improvement which comprises starting the hydrolysis reaction of the cinnamate ester with the alkali by use of water as a solvent in a heterogeneous binary-phase liquid system to obtain an aqueous alkaline solution of an alkali cinnamate said hydrolysis reaction being conducted in the absence of any organic solvent, and the concentration of said alkali cinnamate being 1 to 20 weight percent in the aqueous solution, and precipitating the cinnamic acid by conducting an acidifying reaction of said aqueous alkaline solution with a mineral acid so as to keep a pH value of not more than 4 in a resulting liquid, the concentration of the cinnamic acid being 12 to 20 weight percent in the suspension.

2. The method as claimed in claim 1 wherein the temperature of the hydrolysis reaction is 40° to 120° C.

3. The method as claimed in claim 1 wherein the acidifying reaction is conducted by adding the aqueous alkaline solution of the alkali cinnamate obtained by the hydrolysis reaction into the mineral acid.

4. The method as claimed in claim 1 wherein the acidifying reaction is conducted by continuously charging the aqueous alkaline solution of the alkali cinnamate obtained by the hydrolysis reaction and the mineral acid into the acidifying reaction vessel, followed by continuously discharging the resulting liquid containing the cinnamic acid precepitated therein from said reaction vessel.

* * * * *